United States Patent [19]
Lindemans

[11] Patent Number: 5,486,200
[45] Date of Patent: Jan. 23, 1996

[54] AUTOMATIC POSTMORTEM DEACTIVATION OF IMPLANTABLE DEVICE

[75] Inventor: Fredric W. Lindemans, Sittard, Netherlands

[73] Assignee: Medtronic, Inc., Minneapolis, Minn.

[21] Appl. No.: 233,905

[22] Filed: Apr. 28, 1994

[51] Int. Cl.$^6$ .................................................. A61N 1/39
[52] U.S. Cl. ................................... 607/5; 607/9; 607/21
[58] Field of Search ................................. 607/5, 6, 9, 21; 128/736

[56] References Cited

U.S. PATENT DOCUMENTS

| | | |
|---|---|---|
| 3,805,795 | 4/1974 | Denniston et al. ............ 607/6 |
| 3,867,950 | 2/1975 | Fischell . |
| 4,184,493 | 1/1980 | Langer . |
| 4,250,884 | 2/1981 | Hartlaub et al. . |
| 4,556,063 | 12/1985 | Thompson . |
| 4,803,987 | 2/1989 | Calfee . |
| 4,827,933 | 5/1989 | Koning . |
| 4,928,690 | 5/1990 | Heilman . |
| 5,005,574 | 4/1991 | Fearnot et al. ............ 607/21 |
| 5,027,816 | 7/1991 | Cohen . |
| 5,029,582 | 7/1991 | Lekholm ............ 607/21 |
| 5,105,810 | 4/1992 | Collins . |
| 5,163,429 | 11/1992 | Cohen . |
| 5,190,034 | 3/1993 | Sholder . |

*Primary Examiner*—William E. Kamm
*Assistant Examiner*—Jeffrey R. Jastrzab
*Attorney, Agent, or Firm*—Michael J. Jaro; Harold R. Patton

[57] ABSTRACT

A method and apparatus for minimizing the potential for injury due to operation of a body-implantable device during explant manipulation thereof. In one embodiment of the invention, a body-implantable device is provided with a temperature sensor and associated monitor circuit which issues a deactivation signal when the sensed temperature falls below a predetermined threshold level. Provision is made for subsequent reactivation of the device if it is determined, for example, that sensor failure has led to spurious deactivation of the device.

15 Claims, 1 Drawing Sheet

5,486,200

AUTOMATIC POSTMORTEM DEACTIVATION OF IMPLANTABLE DEVICE

FIELD OF THE INVENTION

This invention relates generally to the field of body-implantable medical device systems, and more particularly to circuitry for automatically deactivating such systems upon the death of the patient.

BACKGROUND OF THE INVENTION

A wide variety of human-implantable medical devices for automatically performing various therapeutic and diagnostic functions are known and commercially available. Such devices include pacemakers, cardioverters, defibrillators, and cardiac monitors, as well as neural simulators, drug-administering devices, and the like. The Medtronic, Inc. Model 7217 PCD is one example of an implantable medical device. This device is capable of pacing, cardioverting, and defibrillating a patient's heart through delivery of electrical stimulating pulses. In the case of defibrillation, those stimulating pulses can be very strong, on the order of 35 Joules or 750-volts or so.

Such implantable devices are often powered by an internal battery which permits the device to function continuously over a long period of time, in some cases up to a decade or more. When a patient with an implanted device dies, the device will often be explanted by a pathologist or an undertaker. This is especially important in instances where the body is to be cremated since the device could explode due to extreme heat With more and more patients having devices implanted, the risk that a person will receive a shock during explant manipulations, for example from an implanted defibrillator, is becoming of increasing concern. A shock during explant may arise because the sensing electrodes used to detect arrhythmic events may receive spurious signals caused by the explant manipulations. These spurious signals could cause the device to "believe" an arrhythmic event is occurring and initiate a therapy, i.e. deliver electric shocks. Usually these shocks are delivered through the electrodes. The potential for injurious shock during explant manipulation may be heightened, however, in situations involving so-called "active canister" devices. Those devices deliver electric shocks through both an electrode as well as the device canister itself. Thus even if the explantor is holding only one electrode, while also holding the device itself, electrical shocks may be delivered. One example of such an active canister implantable defibrillator is the Medtronic, Inc. Model 7219 C. This device is presently undergoing clinical trials in the United States.

At present, one manner in which the potential for injury during explant of implantable devices is addressed is through physician's manuals. These manuals instruct that the devices be programmed to an inactive state upon the death of the patient. The explantor, however, may not have the appropriate programming apparatus at their disposal. Moreover, in many cases the explantor will never have seen the physician's manual for the device. Indeed they may not even become aware a device has been implanted until after the autopsy or embalming process has begun.

In order to reduce the potential that electrical stimulating pulses would occur during explant, it would be desirable to provide a mechanism whereby operation of the device is automatically inhibited or deactivated upon the death of the patient.

SUMMARY OF THE INVENTION

The present invention relates to a method and apparatus for automatic postmortem deactivation of an implantable device, for example, an implantable defibrillator.

Providing automatic postmortem deactivation is achieved by sensing a body parameter which changes after death. Through such a sensed change the device may be automatically deactivated. A particular embodiment of the present invention senses temperature as the body parameter. It has been found that temperature sensing is an effective and reliable method for detecting whether a patient has died. In accordance with one aspect of the present invention, therefore, a circuit is provided which automatically deactivates an implantable device when the temperature sensed drops below a predetermined level. In one embodiment of the invention, a solid-state temperature sensor is contained within the canister of an implantable device to facilitate temperature sensing.

The disclosed embodiment of the invention is further provided with circuitry for latching the device into a deactivated state wherein the device is prevented from operating in its usual modes, but wherein the deactivation may be overridden, for example through external transmission of a programming command.

BRIEF DESCRIPTION OF THE DRAWING

The foregoing and other features and aspects of the present invention may be better appreciated with reference to the following detailed description of the invention when read in conjunction with the accompanying FIG. 1, which is a block diagram of an implantable medical device system including postmortem deactivation circuitry in accordance with one embodiment of the present invention.

DETAILED DESCRIPTION OF THE INVENTION

Figure 1:
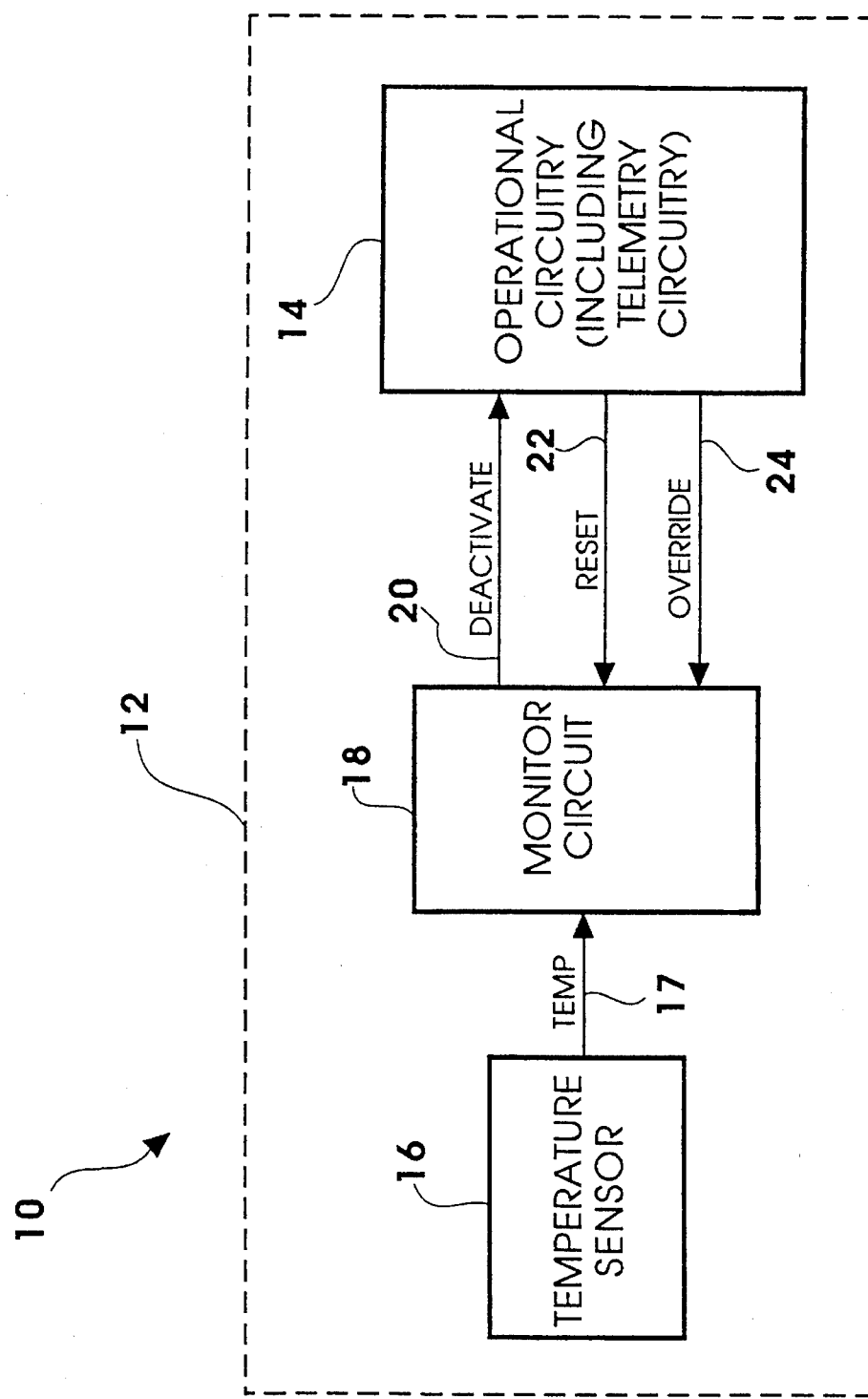

FIG. 1 is a block diagram of an implantable medical device system in accordance with one embodiment of the present invention. For the purposes of the following description, it will be assumed that the invention is being practiced in the context of an implantable defibrillator, such as the Medtronic Model 7219 C, discussed above. It is to be understood, however, that the present invention may be advantageously practiced in conjunction with any number of different types of implantable devices. Moreover, while the specific embodiment illustrated is for purposes of deactivating an implantable device to prevent erroneous electrical pulses, the invention itself concerns a system which changes the operation of a device postmortem.

In FIG. 1 implantable device 10 is contained within conductive hermetic enclosure 12 in accordance with conventional practice in the art. Device 10 includes operational circuitry 14 which includes, in the presently disclosed embodiment of the invention, automatic defibrillator circuitry for generating defibrillating pulses to be delivered to a patient's heart (not shown in FIG. 1) upon detection of fibrillation. In accordance with common practice in the art, defibrillation pulses are applied to the heart via one or more conductive implantable leads (also not shown in the FIG.). In addition, canister 12 may also serve as an electrode for application of defibrillation pulses, as previously described.

As will be appreciated by those of ordinary skill in the art, implantable device 10 preferably includes as a part of its operational circuitry 14 a telemetry system for enabling the device to be non-invasively programmed into various operating modes and with various operational parameters. Such telemetry-based programming systems are well-known in the art, as exemplified, for example, in U.S. Pat. No. 4,250,884 to Hartlaub et al., entitled "Apparatus For and Method Of Programming the Minimum Energy Threshold for Pacing Pulses to be Applied to a Patient's Heart," which describes a programming apparatus for communicating via radio-frequency signals with an implanted device, and in U.S. Pat. No. 4,556,063 to Thompson et al., entitled "Telemetry System for a Medical Device," which describes telemetry circuitry and a telemetry protocol for an implantable device programming system. The Hartlaub et al. '884 and Thompson et al. '063 patents are hereby incorporated by reference herein in their respective entireties.

With continued reference to FIG. 1, implantable device 10 further includes a sensor 16 for monitoring the temperature inside enclosure 12. In one embodiment of the invention, sensor 16 is of the solid-state type, such as the LM34, LM35, LM135, LM235, or LM335 series of precision integrated circuit temperature sensors commercially available from National Semiconductor Corporation, Santa Clara, Calif. Other solid-state temperature sensors believed to be suitable for the purposes of practicing the present invention are commercially available. Sensor 16 generates an analog output signal TEMP, the voltage (or current or impedance) level of which reflects the sensed temperature. In one embodiment of the invention, sensor 16 is mounted on an inner surface of hermetic enclosure 12, such that the sensed temperature generally reflects the temperature to which device 10 is exposed. In the case of an implanted device, those of ordinary skill in the art will appreciate that the temperature of the device will be body temperature (98.6° F.).

As shown in FIG. 1, the TEMP signal from sensor 16 is provided to a monitor circuit 18 on line 17. Monitor circuit 18 compares the TEMP signal voltage (or current or impedance) on line 17 with a predetermined threshold level, in order to ascertain whether the temperature reflected by the TEMP signal is above that threshold. If the temperature reflected by the TEMP signal is determined to be below the predetermined threshold, monitor circuit 18 functions to provide a binary DEACTIVATE signal which is provided on line 20 to operational circuitry 14. Upon provision of the DEACTIVATE signal, operational circuitry enters and remains in a deactivated state wherein no further defibrillation pulses are delivered.

Preferably, provision of the DEACTIVATE signal causes a binary value to be latched, either within monitor circuit 18 itself or within operational circuitry 14 such that even if the temperature subsequently rises above the threshold level, operational circuitry 14 will remain in its deactivated state. Provision of the DEACTIVATE signal preferably does not completely disable operational circuitry 14, however, so that it might be possible to subsequently reactivate circuitry 14, for example via a programming command. In this way, device 10 could be reactivated if it is found that provision of the DEACTIVATE signal occurred as a result of something other than the death of the patient, e.g., failure of sensor 16 or monitor circuit 18.

It is believed that those of ordinary skill in the art having the benefit of the present disclosure could, as a matter of routine design and engineering, implement a latch circuit as part of monitor circuit 18 or of operational circuitry 14, such that with the latch in one state, normal device function is enabled and with the latch in a second state, normal device function is inhibited, as previously described. Alternatively, in the case of software-driven programmable devices, software can be made responsive to provision of the DEACTIVATE signal to execute a software subroutine which similarly results in subsequent persistent cessation of the device's normal activity.

While it may be desirable for operational circuitry 14 to remain deactivated where sensed temperature falls below the threshold level but later rises above the threshold level, two situations in particular are contemplated wherein provision of the DEACTIVATE signal could be due to circumstances other than the death of the patient. One situation, noted above, is when device failure associated either with sensor 16 or monitor circuit 18 leads to provision of the DEACTIVATE signal. In such a case, it would be desirable to provide a mechanism whereby the deactivation circuitry itself could be deactivated. To this end, and as shown in FIG. 1, operational circuitry can be programmed to issue an OVERRIDE signal which is applied to monitor circuit 18 on line 24. It is believed that those of ordinary skill in the art would be readily able to design monitor circuit 18 such that it is rendered responsive to provision of the OVERRIDE signal to shut down, thereby preventing subsequent provision of the DEACTIVATE signal.

With regard to the possibility for failure of temperature sensor 16, it is contemplated that some redundancy of design can be introduced, for example, by providing multiple temperature sensors (not shown in the FIG.). Monitor circuit could in that case require the outputs of all sensors to fall below the predetermined threshold before deactivation is triggered, so that failure of only a single sensor would not lead to spurious provision of the DEACTIVATE signal.

Another situation is contemplated wherein the temperature of device 10 is initially lower than the predetermined threshold (and hence the DEACTIVATE signal is provided and latched) but later rises. During shipment of device 10, for example, and prior to implantation, device 10 must be in at least a partially operational state, such that it is capable of responding to programming signals to be activated into a fully operational state. (That is, absent complete battery depletion, hermetically-sealed implantable devices with internal batteries are never completely "off" or deactivated, but must at least be operational enough to be responsive to some programming commands.) During shipment, and prior to implantation, it is likely that the temperature of device 10 will be below the predetermined threshold level such that monitor circuit would tend to provide the DEACTIVATE signal.

Once implanted and allowed to reach body temperature, monitor circuit 18 would, of course, disable the DEACTIVATE signal. However, if provision of DEACTIVATE causes a latched transition within monitor circuit 18 or within operational circuitry 14 (as previously described), subsequent increases in the sensed temperature above the threshold level would not necessarily result in reactivation of operational circuitry 14.

Those of ordinary skill in the art will appreciate that if provision of the DEACTIVATE signal is latched within operational circuitry, the latch could be reset with an externally transmitted programming command. Alternatively, for software-driven device operation, resumption of normal device functionality can be similarly realized with an externally transmitted programming command. If provision of the DEACTIVATE signal is latched within monitor circuit 18, however, monitor circuit 18 must be rendered responsive to a command from operational circuitry to reset the state of the deactivation latch. To this end, and as shown in FIG. 1, operational circuitry 14 can issue a RESET signal, conveyed to monitor circuit 18 on line 22, to cause monitor circuit to reset the state of its deactivation latch. It is contemplated that it may be preferable to prevent monitor circuit 18 from subsequently re-providing the DEACTIVATE signal for some predetermined delay period. In this way, the deactivation state could be reset prior to or immediately upon implantation of the device (i.e., before the device's temperature has had an opportunity to reach body temperature), while the delay period would prevent the device from being deactivated before the temperature of the device has had an opportunity to reach body temperature.

Regarding the temperature threshold below which device deactivation is triggered, it is presently contemplated by the inventor that a threshold of between 80° to 85° F. will be suitable for the purposes of practicing the present invention, although this value could of course be higher or lower depending upon the particular application of the invention. Indeed, the deactivation temperature threshold could be among the programmable values selectable by the physician or clinician at the time of implantation, as would be apparent to those of ordinary skill in the art.

From the foregoing description the invention, it should be apparent that a method and apparatus for postmortem deactivation of an body-implanted device has been disclosed, such that the potential for injury due to continued operation of the device during explant manipulation is reduced.

Although a specific embodiment of the invention has been described herein, this has been done for the purposes of illustration only and is not intended to be limiting with regard to the scope of the invention. It is contemplated that various substitutions, alterations, and/or modifications, including but not limited to those specifically noted herein, may be made without departing from the spirit and scope of the invention as defined in the appended claims, which follow.

For example, it has been noted herein that the present invention may be advantageously practiced in conjunction with types of implantable devices other than defibrillators. Furthermore, several areas of what are believed to be routine design options exist in connection with the practice of the present invention. For example, the latching of the provided DEACTIVATION signal can occur within various operational components of an implanted device, as described above. For software-based devices, "latching" of the device into a persistent deactivated state is accomplished by virtue of appropriate programming. Provisions may or may not be necessary or desired in a particular application of the invention for overriding or deactivating the deactivation circuitry, for example, via a programming command. Overriding or resetting of the deactivation circuitry may be permanent (e.g., when sensor failure has resulted in spurious provision of the DEACTIVATE signal) or temporary (e.g., when the device has just been implanted and has not reached body temperature). Moreover, the temperature threshold below which deactivation occurs may vary from application to application, and may itself be a programmable parameter for the device.

Although temperature has been described herein as an effective and reliable indicator of whether a patient has died, it is contemplated that detection and monitoring of other physiological parameters which are known to exhibit some change at the time of a patient's death (e.g., physical activity, electrical activity, biochemical activity or the like) may be performed for this purpose. Temperature monitoring is believed to be particularly desirable, since, in the absence of sensor failure, the likelihood of false positive indications of death is small, and the circuitry necessary for monitoring the temperature is simple and consumes little power.

Finally, while the specific embodiment illustrated is for purposes of deactivating an implantable device postmortem to prevent erroneous electrical pulses, the invention itself is more general and concerns any system which changes the operation of a device postmortem, as may be appreciated in the following claims.

What is claimed is:

1. A postmortem deactivation circuit for a body-implantable medical device which is automatically functional to deliver treatment, comprising:

an operational circuit to control the body-implantable medical device and direct delivery of treatment;

a sensor providing an output signal having a level which varies according to a physiological parameter known to change at time of death wherein said physiological parameter is body temperature;

a monitor circuit coupled to said operational circuit, said monitor circuit further coupled to said sensor to receive said output signal, said monitor circuit responsive to said output signal varying below a predetermined threshold to provide a deactivation signal to said operational circuit and suspend said delivery of treatment.

2. A circuit in accordance with claim 1, wherein said predetermined threshold is in a range between 80° to 85° F.

3. A circuit in accordance with claim 1, further comprising a latching circuit coupled to the operational circuit, said latching circuit responsive to provision of said deactivation signal to make a transition from a first latch state to a second latch state.

4. A circuit in accordance with claim 1, wherein said said treatment comprises electrical defibrillation pulses.

5. A method for postmortem deactivation of a body-implantable device, comprising the steps of:

(a) generating a sensor output signal having a level which varies in accordance with body temperature;

(b) monitoring said sensor output signal;

(c) providing a deactivation signal in response to said output signal level falling below a predetermined threshold;

(d) applying said deactivation signal to said body-implantable device to cause deactivation of said device.

6. A method in accordance with claim 4 wherein said step of providing a deactivation signal in response to said output signal level falling below a predetermined threshold comprises providing a deactivation signal in response to said output signal level falling below a temperature in a range between 80° and 85° F.

7. An automatic implantable defibrillator, comprising:

operational circuitry for generating electrical cardiac stimulating pulses in response to cardiac malfunction, said operational circuitry having a control signal input for receiving a deactivation signal;

a sensor, for generating an output signal having a level which varies according to a physiological parameter known to change at time of death wherein said physiological parameter is body temperature;

a monitor circuit, coupled to said sensor and to said operational circuitry control signal input, said monitor circuit responsive to said sensor output signal varying beyond a predetermined threshold level to provide said deactivation signal at said control signal input to suspend generation of electrical cardiac stimulating pulses.

8. An automatic implantable defibrillator in accordance with claim 7, wherein said predetermined threshold level is in a range between 80° and 85° F. and said monitor circuit provides said deactivation signal when said sensor output signal reflects a temperature below said predetermined threshold.

9. An automatic implantable defibrillator in accordance with claim 7, further comprising:

a latch circuit coupled to said monitor circuit, responsive to provision of said deactivation signal to make a transition from a first latch state to a second latch state.

10. An automatic implantable defibrillator in accordance with claim 7, wherein said monitor circuit has an override signal input coupled to said operational circuitry for receiving an override signal from said operational circuitry, said monitor circuit responsive to provision of said override signal to thereafter not provide said deactivation signal.

11. An automatic implantable defibrillator comprising:

a pulse generator, the pulse generator generating electrical stimulation pulses in response to a sensed cardiac arrythmia, the pulse generator having a deactivation signal input for receiving a deactivation signal;

a body temperature sensor, the temperature sensor generating an output signal corresponding to a sensed body temperature;

a monitor, the monitor coupled to the body temperature sensor and to the deactivation signal input, the monitor providing a deactivation signal to the deactivation signal input to suspend generation of electrical stimulation pulses when the output signal varies beyond a predetermined threshold level.

12. An automatic implantable defibrillator in accordance with claim 11, wherein the predetermined threshold level is in a range between 80° and 85° F.

13. An automatic implantable defibrillator in accordance with claim 11 wherein the monitor provides the deactivation signal when the output signal reflects a body temperature below the predetermined threshold.

14. An automatic implantable defibrillator in accordance with claim 13, wherein the predetermined threshold level is in a range between 80° and 85° F.

15. An automatic implantable defibrillator in accordance with claim 11, further comprising a latch coupled to the monitor, the latch responding to the deactivation signal to latch from a first latch state to a second latch state.

* * * * *